US006437169B1

(12) United States Patent
Ito et al.

(10) Patent No.: US 6,437,169 B1
(45) Date of Patent: Aug. 20, 2002

(54) 1-NAPHTHOL COMPOUND AND METHOD FOR PREPARING COMPOUND HAVING ACIDIC PROTON USING THE SAME

(75) Inventors: Takayuki Ito; Koji Takaku, both of Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/597,787

(22) Filed: Jun. 19, 2000

Related U.S. Application Data

(63) Continuation-in-part of application No. 09/293,179, filed on Apr. 16, 1999, now Pat. No. 6,107,016, and a continuation-in-part of application No. 09/577,497, filed on May 24, 2000, now Pat. No. 6,194,131.

(30) Foreign Application Priority Data

| | | |
|---|---|---|
| Apr. 16, 1998 | (JP) | 10-106796 |
| Dec. 18, 1998 | (JP) | 10-375832 |
| Mar. 1, 1999 | (JP) | 11-052732 |
| May 24, 1999 | (JP) | 11-143327 |

(51) Int. Cl.[7] ...................... C07C 271/44; C07D 249/18

(52) U.S. Cl. ............................ 560/27; 560/28; 560/29; 548/142; 548/152; 548/251; 548/257; 548/266.8; 548/291; 548/374.1

(58) Field of Search ............................ 560/27, 28, 29; 548/142, 152, 251, 257, 291, 266.8, 374.1

(56) References Cited

U.S. PATENT DOCUMENTS

| | | |
|---|---|---|
| 3,245,795 A | 4/1966 | Gaspar |
| 3,443,940 A | 5/1969 | Bloom et al. |
| 3,751,406 A | 8/1973 | Bloom |
| 3,958,993 A | 5/1976 | Fujiwhara et al. |
| 4,482,629 A | 11/1984 | Nakagawa et al. |
| 4,985,351 A | 1/1991 | Matejec et al. |
| 5,151,343 A | 9/1992 | Begley et al. |
| 6,054,257 A | 4/2000 | Boff et al. |

FOREIGN PATENT DOCUMENTS

| | | |
|---|---|---|
| DE | 3615232 | * 11/1987 |
| EP | 0950922 A1 | 10/1999 |
| JP | 59171955 | 9/1984 |
| JP | 1129252 | 5/1989 |

* cited by examiner

*Primary Examiner*—Shailendra Kumar
(74) *Attorney, Agent, or Firm*—Birch, Stewart, Kolasch & Birch, LLP

(57) ABSTRACT

1. A 1-naphthol compound represented by formula (I) below:

(I)

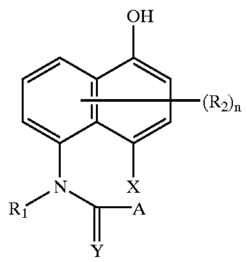

wherein A represents the moiety of a compound having an acidic proton the pKa of a corresponding protonated form (AH) of which is 0 to 14, $R_1$ represents an aliphatic group, aryl group, or heterocyclic group, $R_2$ represents a substituent, n represents an integer of 0 to 5, X represents a hydrogen atom, halogen atom, $R_{11}$—, $R_{11}O$—, $R_{11}S$—, $R_{11}OCOO$—, $R_{12}COO$—, $R_{12}(R_{13})NCOO$—, $R_{12}CON(R_{13})$—, —NO, —$NO_2$, or —N═N—$R_{11}$, wherein $R_{11}$ represents an aliphatic group, aryl group, or heterocyclic group, and each of $R_{12}$ and $R_{13}$ independently represents a hydrogen atom, aliphatic group, aryl group, or heterocyclic group, and Y represents an oxygen atom or sulfur atom.

18 Claims, No Drawings

1-NAPHTHOL COMPOUND AND METHOD FOR PREPARING COMPOUND HAVING ACIDIC PROTON USING THE SAME

CROSS-REFERENCE TO RELATED APPLICATIONS

This is a Continuation-in-Part application of U.S. patent application Ser. No. 09/293,179, filed Apr. 16, 1999 now U.S. Pat. No. 6,107,016; and of U.S. patent application Ser. No. 09/577,497, filed May 24, 2000, now U.S. Pat. No. 6,194,131, the entire contents of which are incorporated herein by reference.

This application is based upon and claims the benefit of priority from the prior Japanese Patent Application No. 10-106796, Apr. 16, 1998; No. 10-375832, Dec. 18, 1998; No. 11-052732, Mar. 11 1999; and No. 11-143327, May 24, 1999, the entire contents of which are incorporated herein by reference.

BACKGROUND OF THE INVENTION

The present invention relates to a naphthol derivative (to be also referred to as a "1-naphthol compound" hereinafter) which functions as a precursor of a compound having an acidic proton, and a method for preparing a compound having an acidic proton. More specifically, the present invention relates to a compound which is stable under alkali hydrolysis conditions and can rapidly release a compound having an acidic proton or the dissociated form of the compound when a nucleophilic substituent is introduced to the 4-position of naphthol, and a method for preparing a compound having an acidic proton.

A 1-naphthol compound of the present invention can be used as a compound for releasing a photographically useful compound and the like in a silver halide photosensitive material.

A technique which converts a compound having an acidic proton into a nonprotic compound (to be referred to as a block body hereinafter) for a certain predetermined period and regenerates the compound from this block body by giving a certain type of stimulus at a desired timing, is used in various fields handling organic compounds. The best known is the concept of protection and deprotection in organic synthetic reactions. For example, when a certain type of conversion reaction is to be performed for a compound having an acidic proton, if the desired reaction does not well progress because the acidic proton exists, this portion is once protected by a protective group to perform the desired reaction, and finally deprotection is performed to regenerate the acidic portion. Also, in the field of silver halide photosensitive materials, a technique is known by which the block body of a photographically useful compound having an acidic proton is incorporated in a photographically inert form into a sensitive material and the photographically useful group is released during development (in some cases, only at a portion where the development progresses). Examples are development inhibitor-releasing couplers described in U.S. patent application Ser. No. 4,248,962 and Jpn. Pat. Appln. KOKAI Publication No. 5-313322 and bleaching accelerator-releasing couplers described in Jpn. Pat. Appln. KOKAI Publication No. 61-201247. This technique also has an important meaning as one method of a drug delivery system in the field of medical treatments.

The most generally known block body of a compound having an acidic proton is a compound protected by a carbonyl group, such as A—COR (A represents the moiety of a compound having an acidic proton the pKa of a corresponding protonated form (AH) of which is 0 to 14, and R represents, e.g., an alkyl group, aryl group, alkoxy group, or amino group). In this block body simply protected by a carbonyl group, the AH can be regenerated (deblocked) by hydrolysis under alkaline conditions. However, the stability as a block body and the ease of deblocking have a tradeoff relationship. That is, when the stability as a block body (A—COR) is raised, the deblocking conditions become strict. If the deblocking conditions become strict, it is well possible that the regenerated AH is further hydrolyzed under the deblocking conditions. If this is the case, A—COR cannot substantially be the block body of AH.

As a method of breaking the tradeoff relationship between the stability of the block body of a compound having an acidic proton and the ease of deblocking from this block body, blocking in the form of methoxymethyl ether or benzyl ether is known refer, for example, to PROTECTIVE GROUP IN ORGANIC SYNTHESIS, John Wiley & Sons, Inc., Second Edition pp. 149–150 & 156–158). While these block bodies are stable under alkaline conditions, methoxymethyl ether can be deblocked under relatively moderate acidic conditions. Also, benzyl ether can be readily deblocked under moderate catalitic reducing conditions. However, these block bodies cannot be used for compounds that are unstable under acidic or reducing conditions.

Furthermore, although the development inhibitor-releasing couplers and bleaching accelerator-releasing couplers in the field of silver halide photosensitive materials described above are relatively stable under alkali hydrolysis conditions, they can release development inhibitors and bleaching accelerates only at exposed portions during development. However, in these examples the synthesis of a block body and the ease of deblocking largely depend upon the type of body to be blocked. Also, an azomethine dye is generated in addition to deblocking. Hence, any of these examples is not highly versatile as the block body of a compound having an acidic proton.

BRIEF SUMMARY OF THE INVENTION

It is an object of the present invention to provide a compound effective as the block body of a compound having an acidic proton, which is stable under alkali hydrolysis conditions and can rapidly regenerate a compound having an acidic proton or the dissociated form thereof when a nucleophilic group is introduced to a specific position in a molecule.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The object of the present invention is achieved by a compound represented by formula (I) below:

(I)

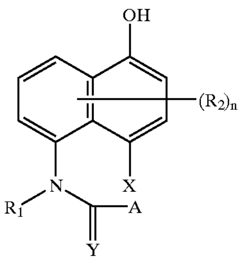

wherein A represents the moiety of a compound having an acidic proton the pKa of a corresponding protonated form (AH) of which is 0 to 14, $R_1$ represents an aliphatic group, aryl group, or heterocyclic group, $R_2$ represents a substituent, n represents an integer of 0 to 5, X represents a hydrogen atom, halogen atom, $R_{11}$—, $R_{11}$O—, $R_{11}$S—, $R_{11}$OCOO—, $R_{12}$COO—, $R_{12}(R_{13})$NCOO—, $R_{12}$CON($R_{13}$)—, —NO, —$NO_2$, or —N═N—$R_{11}$, and Y represents an oxygen atom or sulfur atom. $R_{11}$ represents an aliphatic group, aryl group, or heterocyclic group, and each of $R_{12}$ and $R_{13}$ independently represents a hydrogen atom, aliphatic group, aryl group, or heterocyclic group.

The present invention also provides a method for preparing a compound having an acidic proton in which a nucleophilic group is introduced to the 4-position of a 1-naphthol compound represented by formula (I) above and which is represented by AH by the intramolecular nucleophilic reaction.

Details of a compound represented by formula (I) will be described below.

A represents the moiety of a compound having an acidic proton the pKa of a corresponding protonated form (AH) of which is 0 to 14. Preferably, A represents the moiety of a compound having an acidic proton the pKa of a corresponding protonated form (AH) of which is 2 to 11.

Preferable examples of A are a 6- to 32-carbon, preferably 6- to 22-carbon substituted or nonsubstituted aryloxy group (e.g., phenoxy and naphthyloxy), a 1- to 32-carbon, preferably 1- to 22-carbon substituted or nonsubstituted heterocyclic oxy group (e.g., pyridyloxy and quinolyloxy), a 1- to 32-carbon, preferably 1- to 22-carbon substituted or nonsubstituted alkylthio group (e.g., methylthio, ethylthio, and butylthio), a 6- to 32-carbon, preferably 6- to 22-carbon substituted or nonsubstituted arylthio group (e.g., phenylthio and naphthylthio), a 1- to 32-carbon, preferably 1- to 22-carbon substituted or nonsubstituted heterocyclic thio group (e.g., tetrazolylthio, triazolylthio, oxazolylthio, imidazolylthio, benzimidazolylthio, benzothiazolylthio, and benzoxazolylthio), a 1- to 32-carbon, preferably 1- to 22-carbon substituted or nonsubstituted azole group (e.g., tetrazole, 1,2,3-triazole, 1,2,4-triazole, and benzotriazole), and a 2- to 32-carbon, preferably 2- to 22-carbon substituted or nonsubstituted carbonyloxy group (e.g., acetyloxy and benzoyloxy).

More preferable examples of A are an aryloxy group, heterocyclic oxy group, alkylthio group, arylthio group, heterocyclic thio group, and azole group described above (practical examples of these groups are those enumerated above).

$R_1$ represents an aliphatic group (an aliphatic group means a saturated or unsaturated, chainlike or cyclic, straight-chain or branched, substituted or nonsubstituted aliphatic hydrocarbon group, and has the same meaning in the rest of the document), aryl group, or heterocyclic group.

An aliphatic group represented by $R_1$ is an aliphatic group having preferably 1 to 32, and more preferably, 1 to 22 carbon atoms. Practical examples are methyl, ethyl, vinyl, ethynyl, propyl, isopropyl, 2-propenyl, 2-propynyl, butyl, isobutyl, t-butyl, t-amyl, hexyl, cyclohexyl, 2-ethylhexyl, octyl, 1,1,3,3-tetramethylbutyl, decyl, dodecyl, hexadecyl, and octadecyl. An aryl group represented by $R_1$ is a substituted or nonsubstituted aryl group having preferably 6 to 32, and more preferably, 6 to 22 carbon atoms. Practical examples are phenyl, tolyl, and naphthyl. A heterocyclic group represented by $R_1$ is a substituted or nonsubstituted 3- to 8-membered, preferably 5- or 6-membered heterocyclic group having preferably 1 to 32, and more preferably, 1 to 22 carbon atoms. Practical examples are 2-furyl, 2-pyrolyl, 2-thienyl, 3-tetrahydrofuranyl, 4-pyridyl, 2-pyrimidinyl 2-(1,3,4-thiadiazolyl), 2-benzothioazolyl, 2-benzoxazolyl, 2-benzoimidazolyl, 2-benzoselenazolyl, 2-quinolyl, 2-oxazolyl, 2-thiazolyl, 2-selenazolyl, 5-tetrazolyl, 2-(1,3,4-oxadiazolyl), and 2-imidazolyl.

$R_1$ is preferably a 1- to 22-carbon aliphatic group, and more preferably, a 1- to 16-carbon aliphatic group.

$R_2$ represents a substituent, and n represents an integer of 0 to 5. If n represents an integer of 2 or more, these $R_2$'s can be the same or different. Also, adjacent $R_2$'s can form a ring.

Examples of a substituent represented by $R_2$ or a substituent suited to the groups described above and groups explained below are a halogen atom (e.g., a fluorine atom, chlorine atom, bromine atom, and iodine atom), hydroxyl group, carboxyl group, sulfo group, cyano group, nitro group, alkyl group (e.g., methyl, ethyl, and hexyl), fluoroalkyl group (e.g., trifluoromethyl), aryl group (e.g., phenyl, tolyl, and naphthyl), heterocyclic group (e.g., a heterocyclic group described in the explanation of $R_1$), alkoxy group (e.g., methoxy, ethoxy, and octyloxy), aryloxy group (e.g., phenoxy and naphthyloxy), alkylthio group (e.g., methylthio and butylthio), arylthio group (e.g., phenylthio), amino group (e.g., amino, N-methylamino, N,N-dimethylamino, and N-phenylamino), acyl group (e.g., acetyl, propionyl, and benzoyl), alkylsulfonyl or arylsulfonyl group (e.g., methylsulfonyl and phenylsulfonyl), acylamino group (e.g., acetylamino and benzoylamino), alkylsulfonylamino or arylsulfonylamino group (e.g., methanesulfonylamino and benzenesulfonylamino), carbamoyl group (e.g., carbamoyl, N-methylaminocarbonyl, N,N-dimethylaminocarbonyl, and N-phenylaminocarbonyl), sulfamoyl group (e.g., sulfamoyl, N-methylaminosulfonyl, N,N-dimethylaminosulfonyl, and N-phenylaminosulfonyl), alkoxycarbonyl group (e.g., methoxycarbonyl, ethoxycarbonyl, and octyloxycarbonyl), aryloxycarbonyl group (e.g., phenoxycarbonyl and naphthyloxycarbonyl), acyloxy group (e.g., acetyloxy and benzoyloxy), alkoxycarbonyloxy group (e.g., methoxycarbonyloxy and ethoxycarbonyloxy), aryloxycarbonyloxy group (e.g., phenoxycarbonyloxy), alkoxycarbonylamino group (e.g., methoxycarbonylamino and butoxycarbonylamino), aryloxycarbonylamino group (e.g., phenoxycarbonylamino), aminocarbonyloxy group (e.g., N-methylaminocarbonyloxy and N-phenylaminocarbonyloxy), and aminocarbonylamino group (e.g., N-methylaminocarbonylamino and N-phenylaminocarbonylamino).

n is preferably 1 or 2, and more preferably, 1. $R_2$ is preferably a group represented by $R_3$ (to be described later).

X represents a hydrogen atom, halogen atom (e.g., a fluorine atom, chlorine atom, bromine atom, or iodine atom), $R_{11}$—, $R_{11}$O—, $R_{11}$S—, $R_{11}$OCOO—, $R_{12}$COO—, $R_{12}$($R_{13}$)NCOO—, $R_{12}$CON($R_{13}$)—, —NO, —$NO_2$, or —N═N—$R_{11}$, and Y represents an oxygen atom or sulfur atom. $R_{11}$ represents an aliphatic group, aryl group, or heterocyclic group, and each of $R_{12}$ and $R_{13}$ independently represents a hydrogen atom, aliphatic group, aryl group, or heterocyclic group. An aliphatic group, aryl group, and heterocyclic group represented by $R_{11}$, $R_{12}$, and $R_{13}$ have the same meanings as $R_1$.

Preferably, X represents a hydrogen atom, aliphatic group, aliphatic oxy group, aliphatic thio group, or $R_{12}$CON($R_{13}$)—, and Y represents an oxygen atom. More preferably, X represents a hydrogen atom.

A compound represented by formula (I) of the present invention can be preferably represented by formula (II) below, and more preferably represented by formula (III) below:

(II)

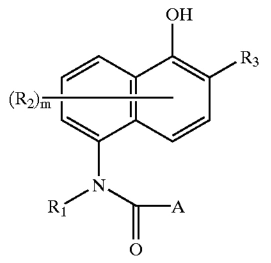

(III)

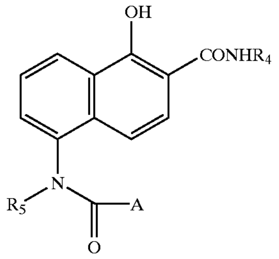

wherein $R_3$ represents a hydrogen atom, halogen atom (e.g., a fluorine atom, chlorine atom, bromine atom, or iodine atom), cyano group, $R_{12}$($R_{13}$)NCO—, or $R_{12}$CON($R_{13}$)—, $R_4$ represents a hydrogen atom or a group having the same meaning as $R_1$, $R_5$ represents an aliphatic group having 1 to 32, preferably, 1 to 22, and more preferably, 1 to 18 carbon atoms, m represents an integer of 0 to 4, and $R_1$, $R_2$, A, $R_{12}$, and $R_{13}$ represent groups having the same meanings as above.

Practical examples of a compound of the present invention will be presented below, but the present invention is not limited to these examples.

(1)

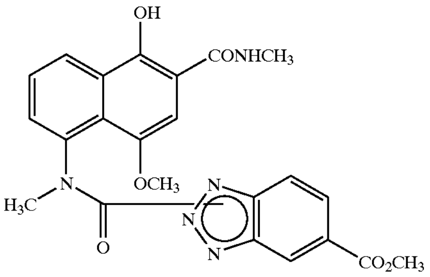

(2)

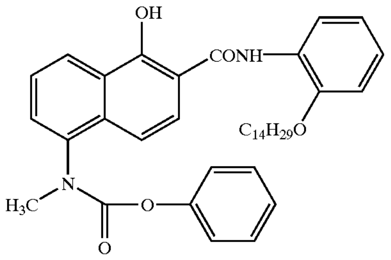

(3)

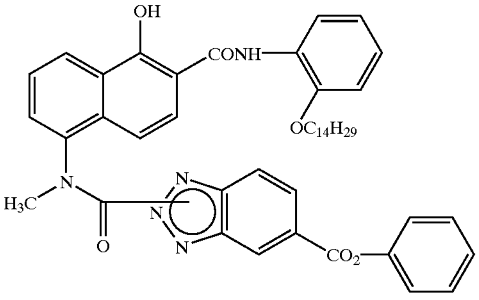

-continued
(4)
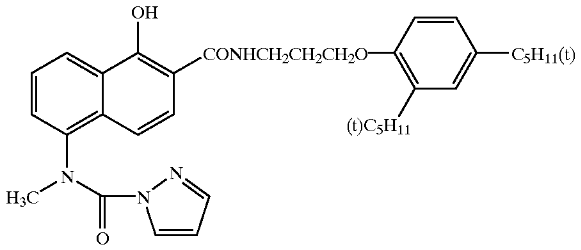
(5)
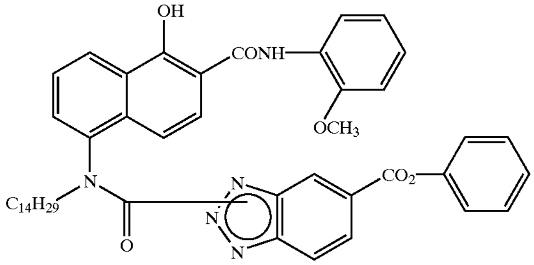
(6)
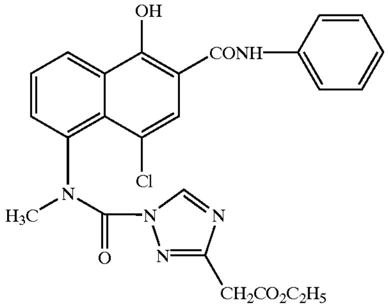
(7)
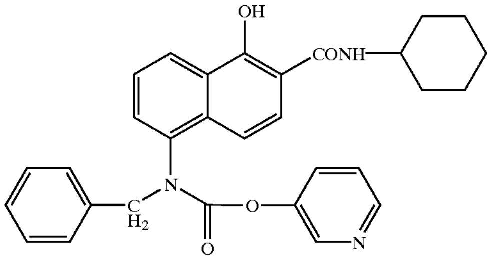
(8)
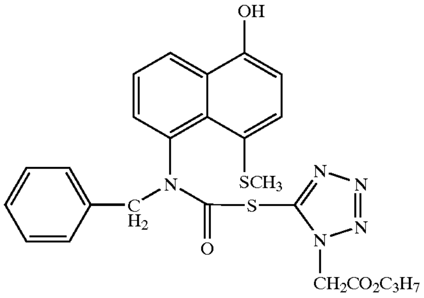
(9)
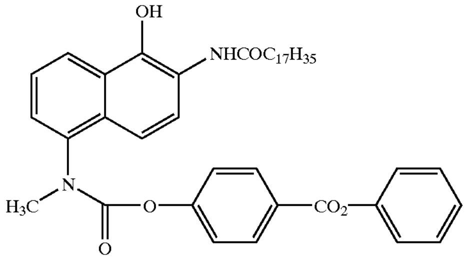
(10)
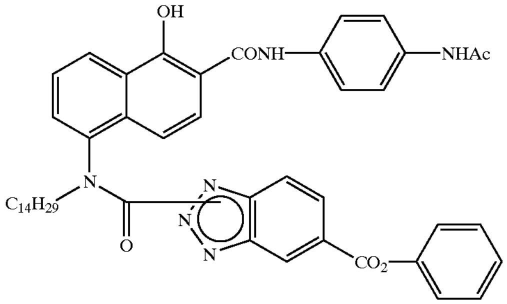
(11)
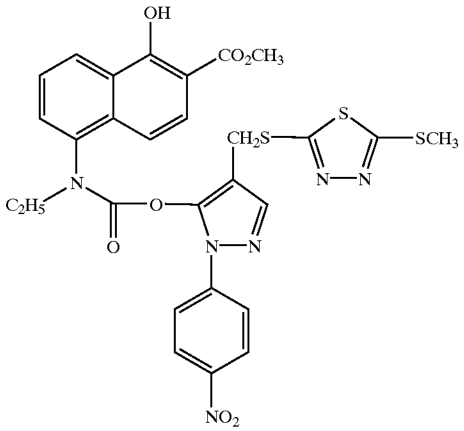
(12)
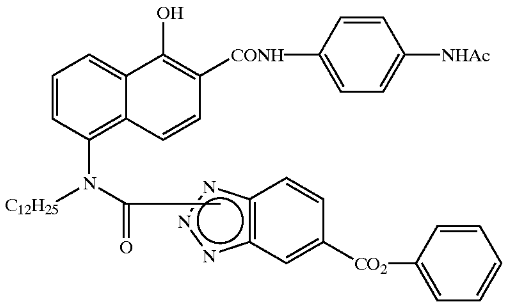

-continued
(13)
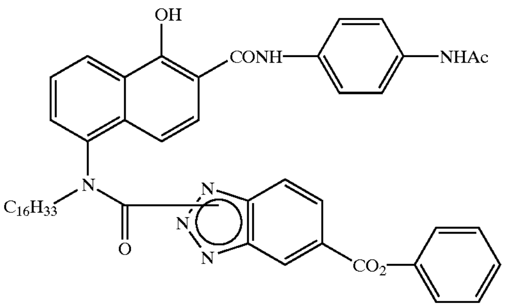
(14)
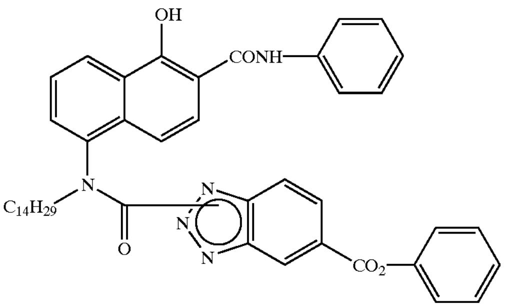
(15)
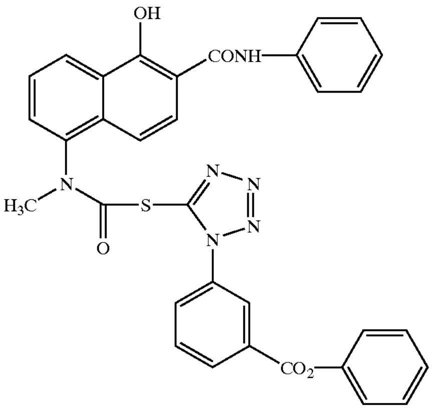
(16)
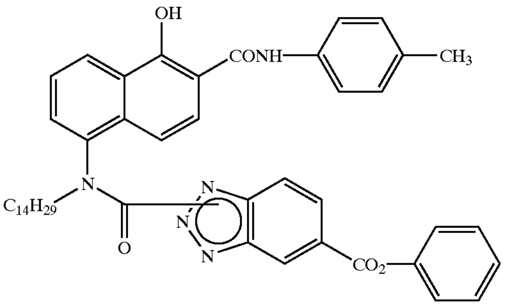
(17)
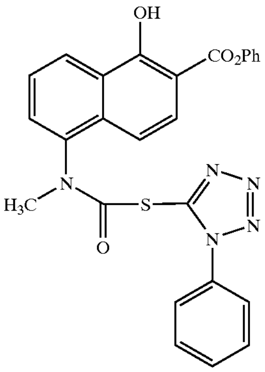
(18)
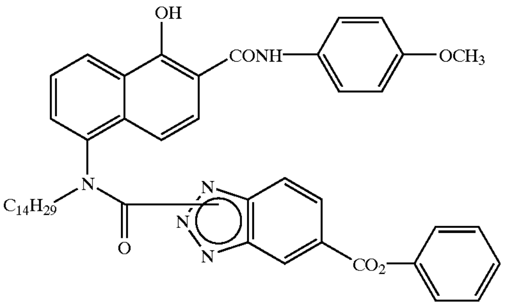
(19)
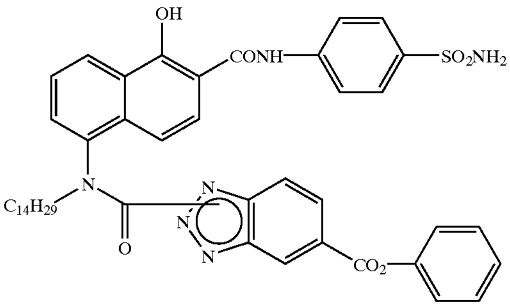
(20)
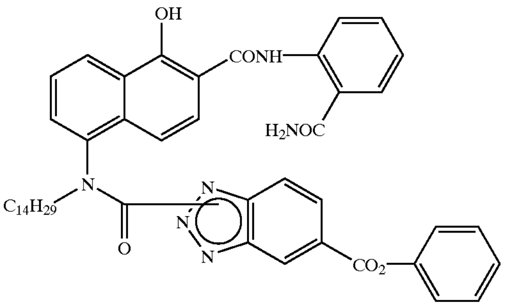

-continued
(21)
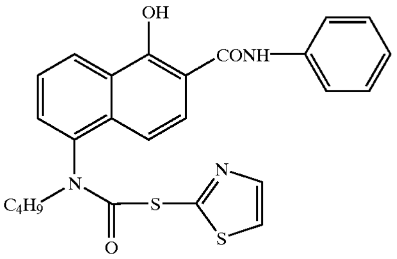
(22)
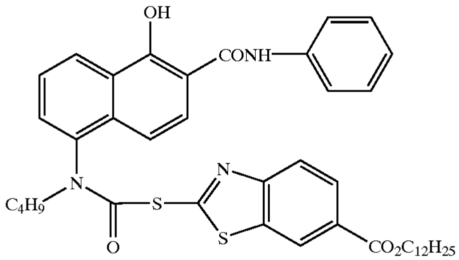
(23)
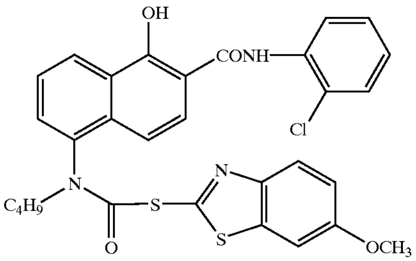
(24)
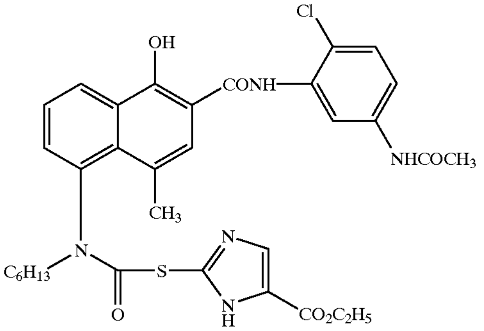
(25)
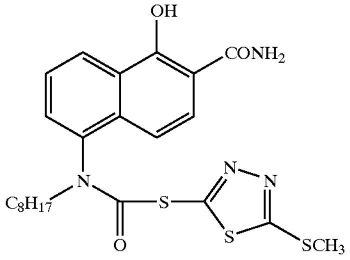
(26)
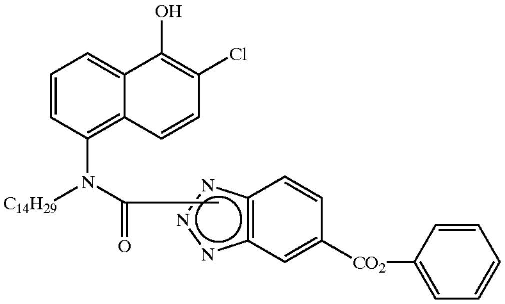
(27)
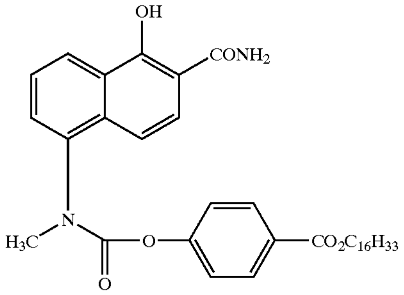
(28)
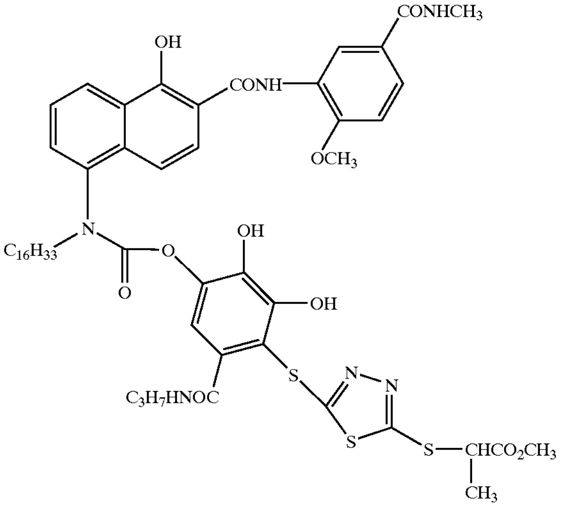
(29)
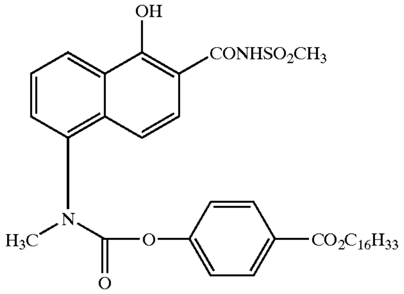

-continued
(30)
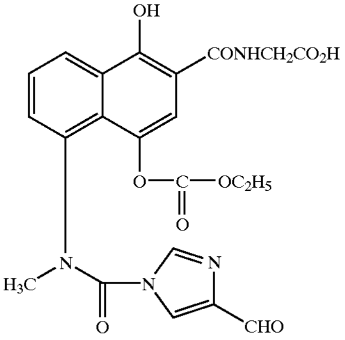
(31)
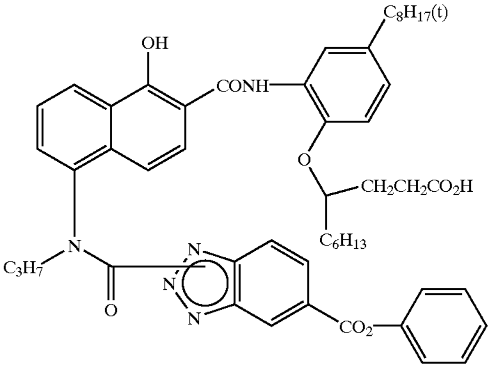
(32)
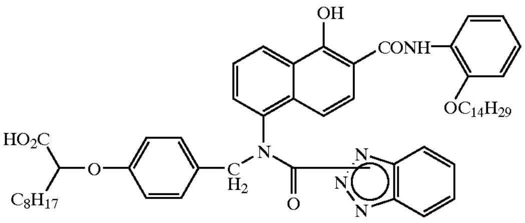
(33)
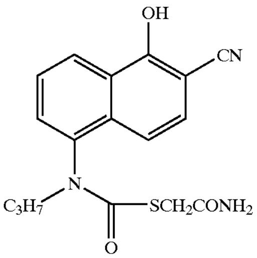
(34)
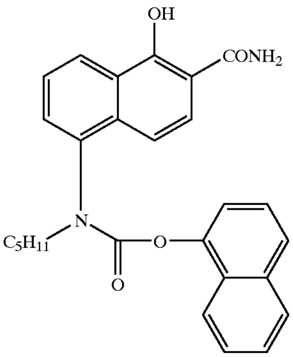
(35)
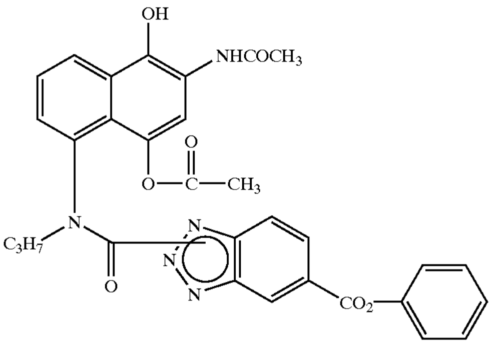
(36)
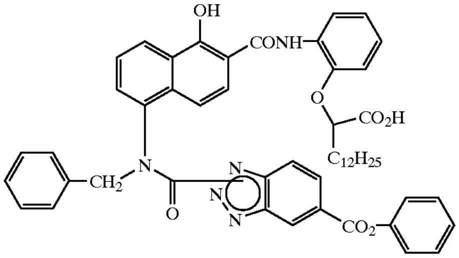
(37)
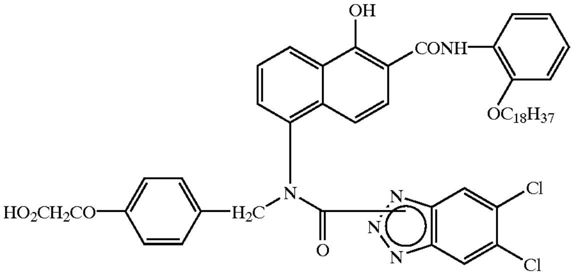
(38)
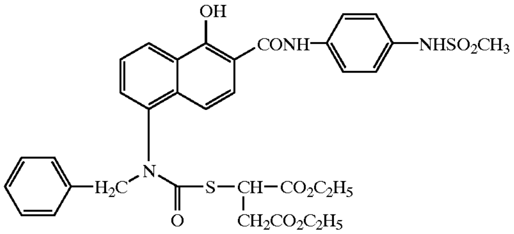
(39)
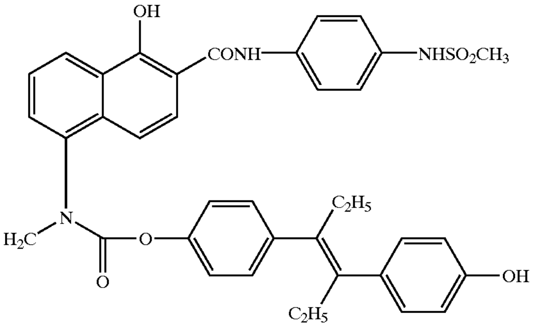

-continued
(40)
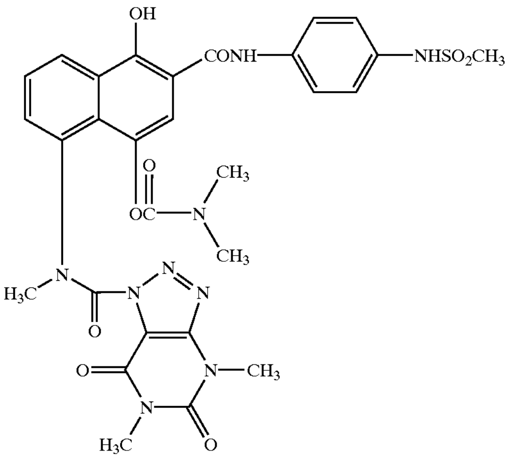
(41)
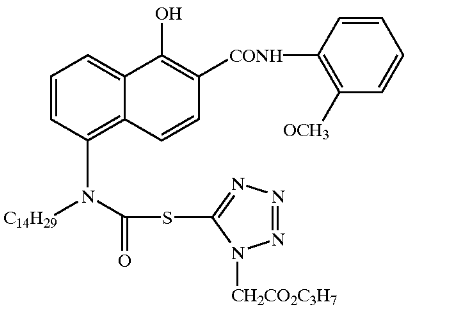
(42)
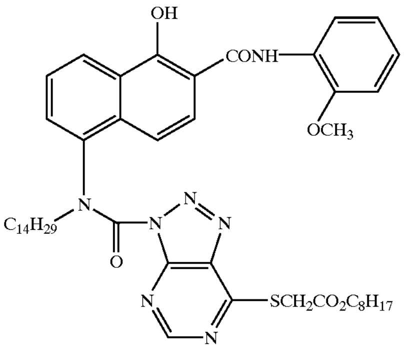
(43)
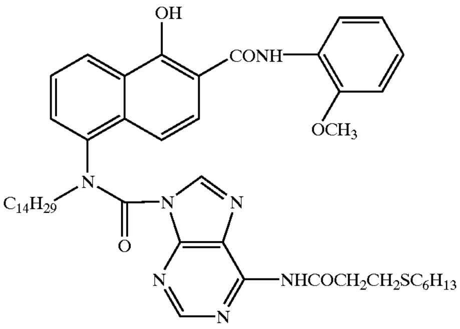
(44)
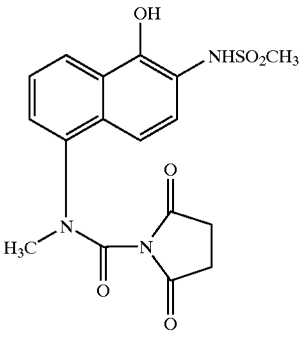
(45)
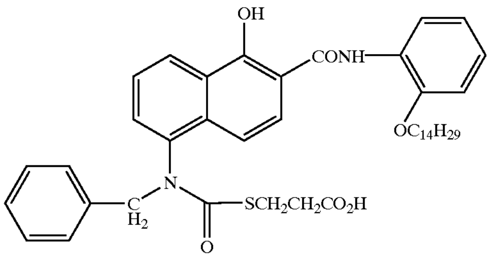
(46)
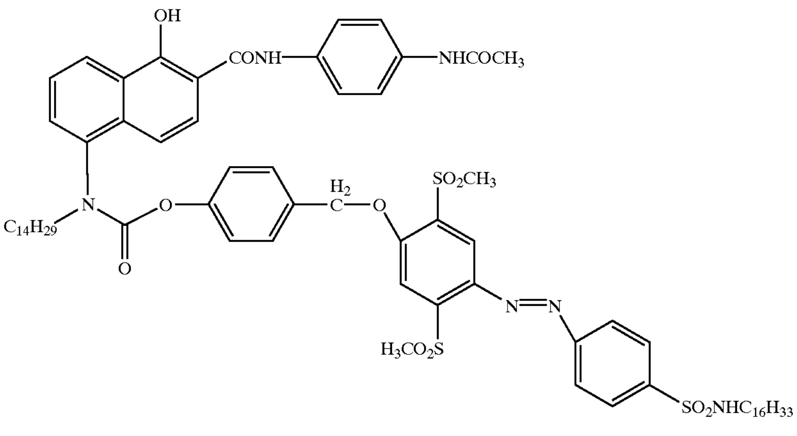

-continued
(47)
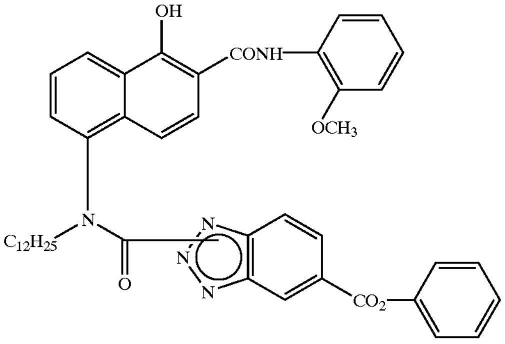
(48)
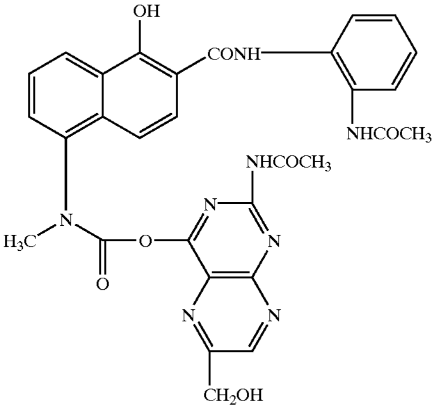
(49)
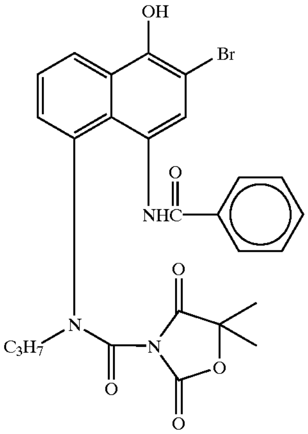
(50)
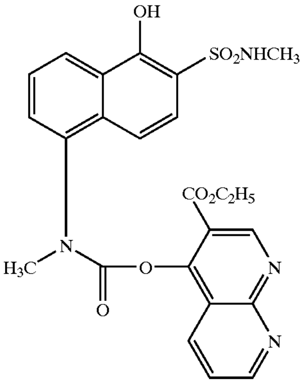
(51)
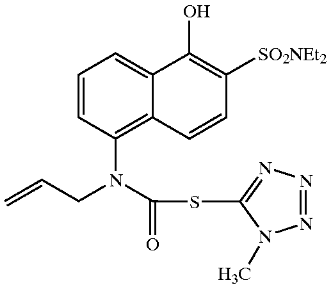
(52)
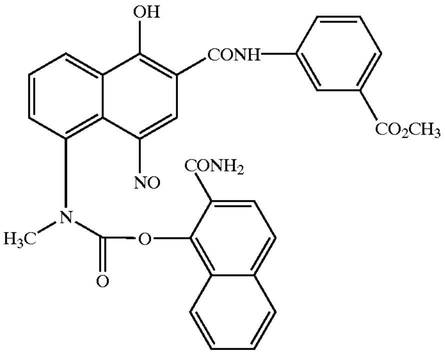
(53)
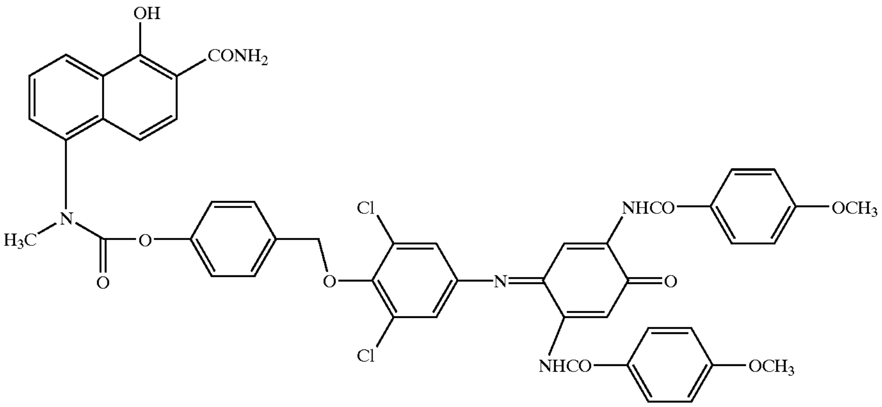

-continued
(54)
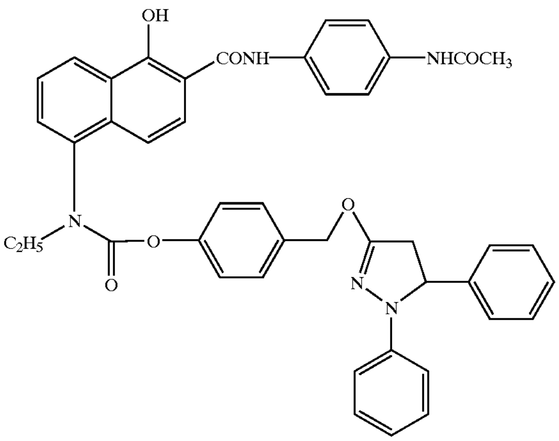
(55)
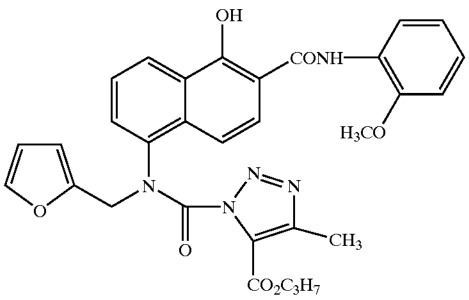
(56)
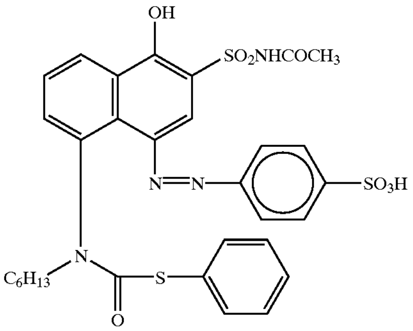
(57)
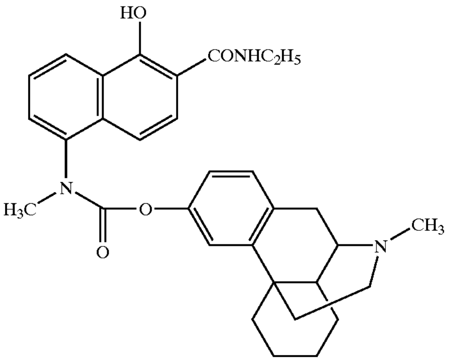
(58)
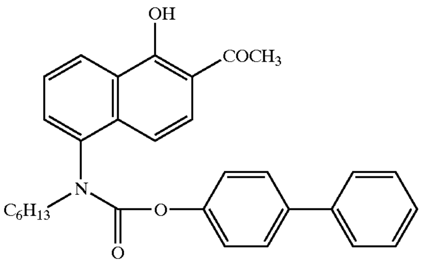
(59)
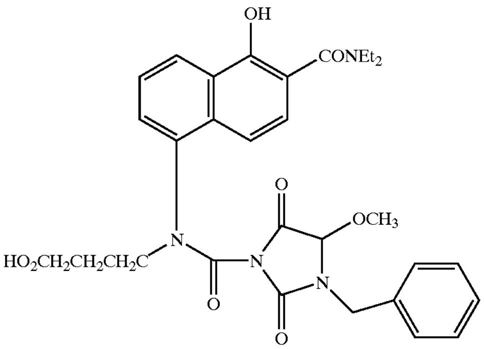
(60)
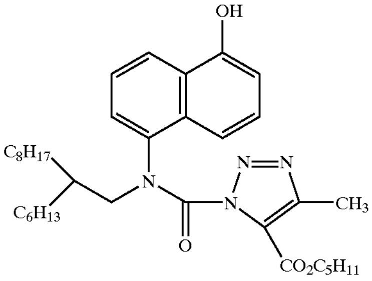
(61)
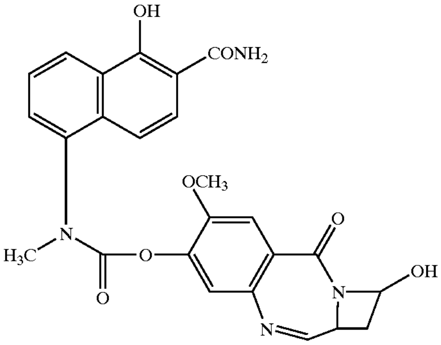

-continued
(62)
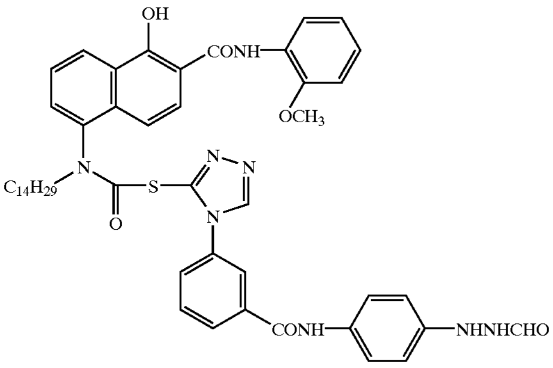
(63)
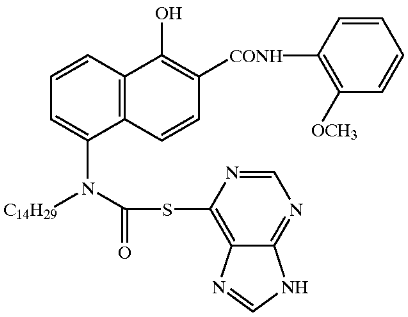
(64)
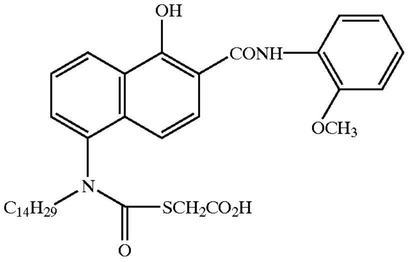
(65)
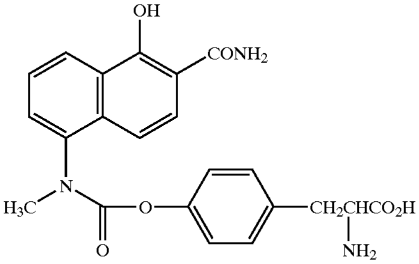
(66)
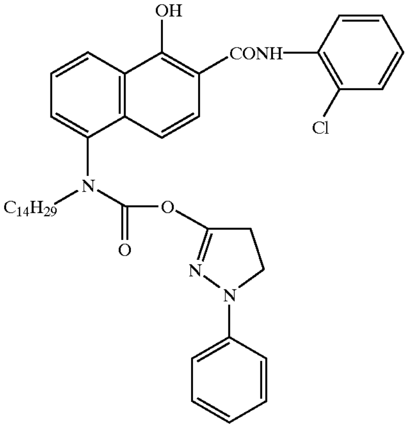
(67)
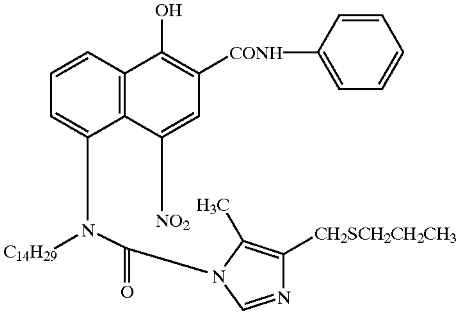
(68)
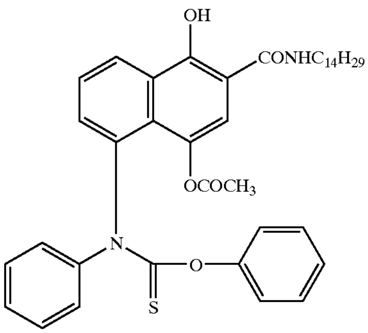
(69)
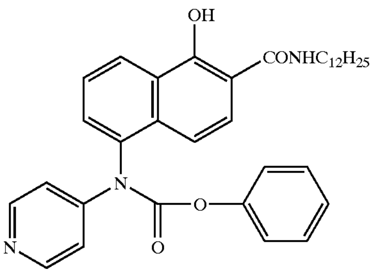

A general synthesis method of a compound of the present invention will be described below.

An acid precursor of the present invention can be readily synthesized by route 1 or route 2 below:

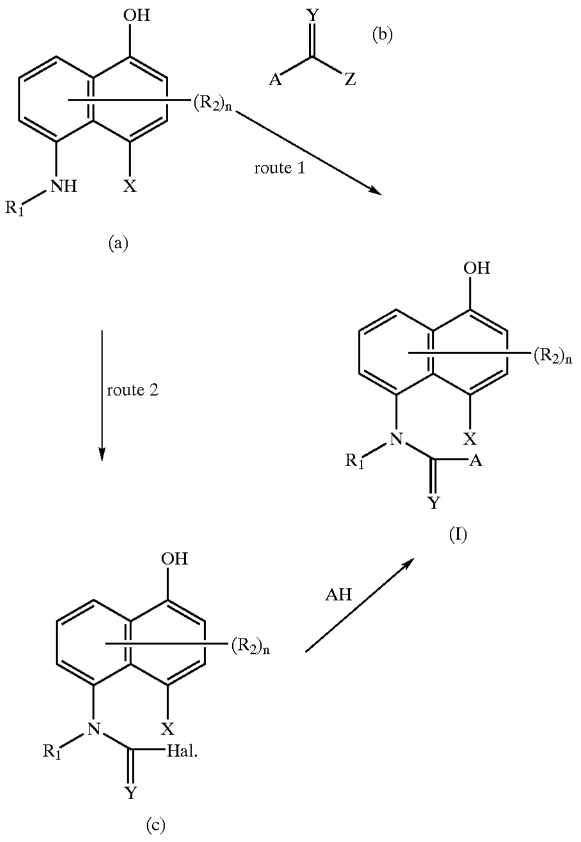

Explanation of Route 1

A compound represented by formula (I) can be synthesized by reacting compounds (a) and (b) (Z represents A, a halogen atom, phenoxy group, or p-nitrophenoxy group, preferably a halogen atom or p-nitrophenoxy group, and more preferably, a chloro atom).

A solvent for the reaction of (a) with (b) is preferably dichloromethane, chloroform, toluene, xylene, hexane, heptane, ethyl acetate, tetrahydrofuran, diethyl ether, acetonitrile, N,N-dimethylacetamide, or N,N-dimethylformamide, and more preferably, dichloromethane, toluene, ethyl acetate, or tetrahydrofuran.

The solvent amount is preferably 1 to 100 times (weight ratio), and more preferably, 3 to 20 times the amount of the compound (a).

Although the reaction of (a) with (b) can be performed with no base, it is preferably performed in the presence of a base. The base for use in the reaction of (a) with (b) is preferably pyridine, α-, β-, or γ-picoline, lutidine, N-methylmorpholine, N,N-dimethylaniline, N,N-diethylaniline, quinoline, sodium bicarbonate, sodium carbonate, potassium bicarbonate, or potassium carbonate, and more preferably, N,N-dimethylaniline, N,N-diethylaniline, or quinoline.

In the reaction of (a) with (b), the reaction temperature is preferably −20° C. to 100° C., and more preferably, 0° C. to 50° C.

In the reaction of (a) with (b), the reaction time is preferably 5 min to 5 hr, and more preferably, 30 min to 2 hr.

The compound (a) can be readily synthesized by the reaction of a corresponding 5-amino-1-naphthol derivative and $R_1$-Hal. (Hal. represents a halogen atom, preferably a bromine atom or iodine atom). The compound (b) can be easily synthesized by the reaction of AH with phosgene, thiophosgene, trichloromethylchloroformate, bis(trichloromethyl) carbonate, phenyl chlorocarbonate, or p-nitrophenyl chlorocarbonate.

The amount of (b) is preferably 0.5 to 2 equivalent times, and more preferably, 0.8 to 1.2 equivalent times the amount of (a). When a base is used, the amount of the base is preferably 0.5 to 10 equivalent times, more preferably, 0.8 to 5 equivalent times, and most preferably, 0.9 to 2 equivalent times the amount of (a).

Explanation of Route 2

A compound represented by formula (I) can be synthesized by once converting the compound (a) into a compound (c) (Hal. represents a halogen atom, preferably a chlorine atom) and reacting this compound (c) with the compound AH.

As a reagent for converting (a) into (c), it is possible to use, e.g., phosgene, thiophosgene, trichloromethylchloroformate, or bis(trichloromethyl) carbonate.

A solvent for the reaction of converting (a) into (c) is preferably dichloromethane, chloroform, toluene, xylene, hexane, heptane, ethyl acetate, tetrahydrofuran, or diethyl ether, and more preferably, dichloromethane, toluene, ethyl acetate, or tetrahydrofuran.

The solvent amount is preferably 1 to 100 times (weight ratio), and more preferably, 3 to 20 times the amount of the compound (a).

The reaction of converting (a) into (c) can be performed with no base or in the presence of a base. The base for use in the reaction of converting (a) into (c) is preferably pyridine, α-, β-, or γ-picoline, lutidine, N-methylmorpholine, N,N-dimethylaniline, N,N-diethylaniline, or quinoline, and more preferably, N,N-dimethylaniline, N,N-diethylaniline, or quinoline.

In the reaction of converting (a) into (c), the reaction temperature is preferably −20° C. to 100° C., and more preferably, 0° C. to 50° C.

In the reaction of converting (a) into (c), the reaction time is preferably 5 min to 5 hr, and more preferably, 30 min to 2 hr.

The amount of the reagent for converting (a) into (c) is preferably 0.5 to 2 equivalent times, and more preferably, 0.8 to 1.2 equivalent times the amount of (a).

A solvent for the reaction of (c) with AH is preferably dichloromethane, chloroform, toluene, xylene, chlorobenzene, hexane, heptane, ethyl acetate, tetrahydrofuran, diethyl ether, acetonitrile, N,N-dimethylacetamide, or N,N-dimethylformamide, and more preferably, dichloromethane, toluene, xylene, chlorobenzene, ethyl acetate, or tetrahydrofuran.

The solvent amount is preferably 1 to 100 times (weight ratio), and more preferably, 3 to 20 times the amount of the compound (c).

The reaction of (c) with AH can be performed with no base or in the presence of a base. The base for use in the reaction of (c) with AH is preferably triethylamine, diisopropylethylamine, sodium methoxide, sodium t-butoxide, potassium t-butoxide, sodium hydride, pyridine, α-, β-, or γ-picoline, lutidine, N-methylmorpholine, N,N-dimethylaniline, N,N-diethylaniline, quinoline, sodium bicarbonate, sodium carbonate, potassium bicarbonate, or potassium carbonate, and more preferably, triethylamine, diisopropylethylamine, sodium methoxide, sodium t-butoxide, potassium t-butoxide, sodium hydride, pyridine, α-, β-, or γ-picoline, or lutidine.

In the reaction of (c) with AH, the reaction temperature is preferably −20° C. to 170° C., more preferably, 0° C. to 150° C., and much more preferably, 20° C. to 120° C.

The amount of AH is preferably 0.5 to 10 equivalent times, more preferably, 0.8 to 5 equivalent times, and much more preferably 0.9 to 2 equivalent times the amount of (c). The amount of the base is preferably 0.5 to 2 equivalent times, and more preferably, 0.8 to 1.2 equivalent times the amount of AH.

In the reaction of (c) with AH, the reaction time is preferably 5 min to 10 hr, and more preferably, 30 min to 5 hr.

A method of regenerating a compound (AH) having an acidic proton from a compound of the present invention will be described below.

As indicated by a formula presented below, a 1-naphthol derivative of the present invention can rapidly release $A^-$ (or AH) along with an intramolecular ring closure reaction when a nucleophilic substituent is introduced to its 4-position by some method. The nucleophilic substituent is preferably —$NHR_6$ ($R_6$ represents a hydrogen atom or a group having the same meaning as $R_1$ described previously), —OH, or —SH, and more preferably, —$NHR_6$ or —OH.

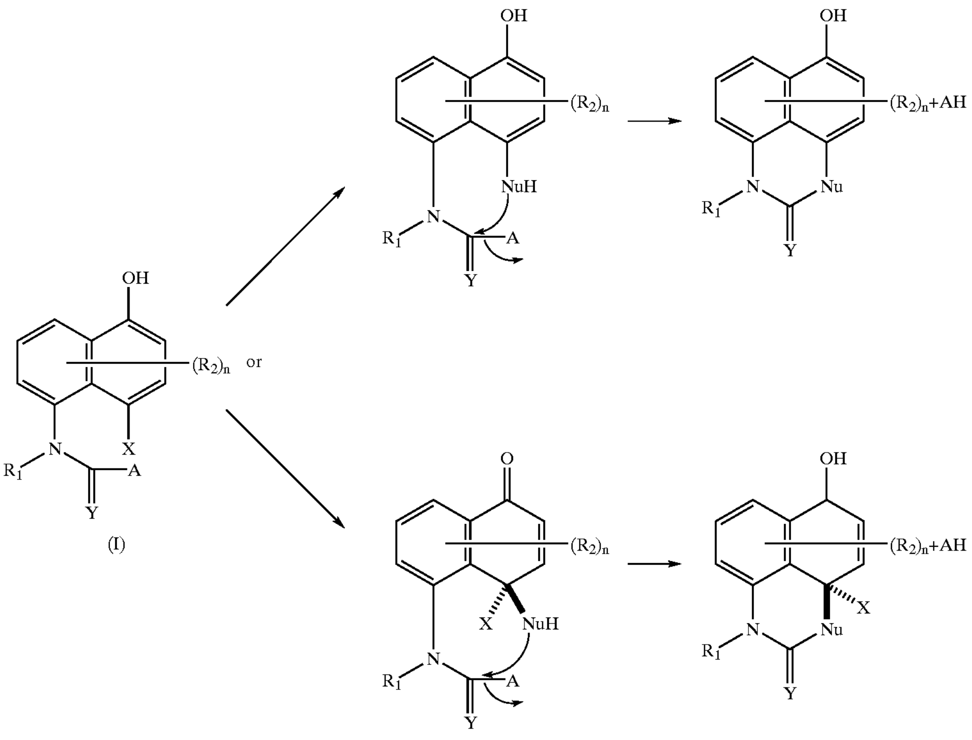

or (I)

The following methods are possible as a method of introducing the nucleophilic substituent, but the present invention is not limited to these methods.

(1) If X represents —NO, —$NO_2$, or —N═N—$R_{11}$ in formula (I), they can be converted into —$NH_2$ by a general reducing reaction (e.g., a method described in "New Experimental Chemistry Course 14", Maruzen K. K., pp. 1332–1336).

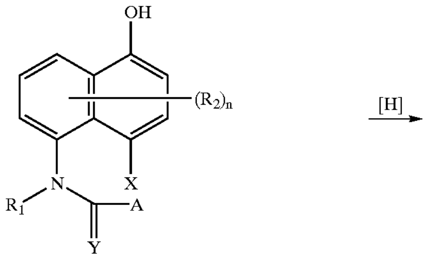

[H]

X = —NO, —$NO_2$, —N═N—$R_{11}$

-continued

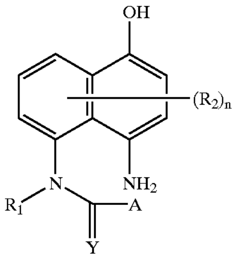

(2) If X represents $R_{11}O$—, $R_{11}OCOO$—, $R_{12}COO$—, or $R_{12}(R_{13})NCOO$— in formula (I), the $R_{11}$—O bond can be cut by using a Lewis acid such as aluminum chloride or boron tribromide or can be converted into —OH by performing decarbonylation by hydrolysis.

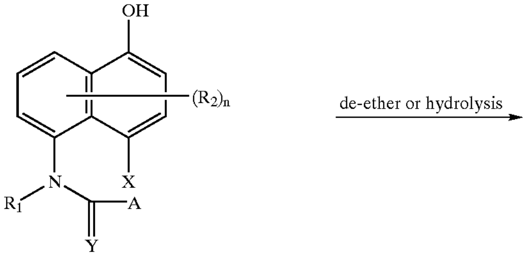

$X = R_{11}O—, R_{11}OCOO—, R_{12}COO—, R_{12}(R_{13})NCOO—$

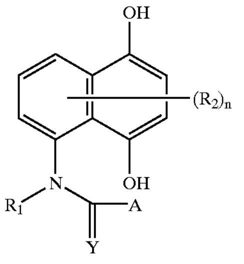

(3) Regardless of X in formula (I), an amino group can be introduced by reaction with the oxidized form of a developing agent used in a silver halide photosensitive material (e.g., phenylenediamine-based and aminophenol-based developing agents described in U.S. Pat. Nos. 2,193,015, 2,592,364, and 5,240,821 and Jpn. Pat. Appln. KOKAI Publication No. 48-64933, sulfonylhydrazine-based developing agents described in European Patent Nos. 545491A1 and 565165A1, carbamoylhydrazine-based developing agents described in Jpn. Pat. Appln. KOKAI Publication Nos. 8-286340, 9-152702, and 9-211818, and 4-aminoantipyrine; preferably, p-phenylenediamine-based developing agents such as 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, and 3-methyl-4-amino-N-ethyl-N-β-methoxyethylaniline). The following formula indicates an example in which an arylamino group is introduced to the 4-position of naphthol by the reaction of a compound represented by formula (I) with a p-phenylenediamine-based developing agent in the oxidized form (each of $R_{31}$, $R_{32}$, and $R_{33}$ independently represents an aliphatic group).

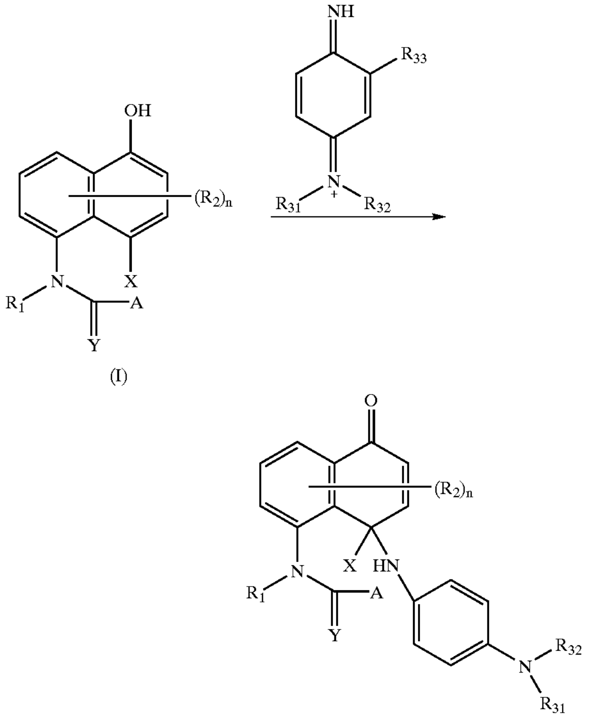

(I)

(4) If X is a hydrogen atom in formula (I), a hydroxyl group can be introduced by an oxidation reaction (e.g., a method described in "New Experimental Chemistry Course 15", Maruzen K. K., pp. 638–645, or a reaction using an enzyme in a living body). If X is a hydrogen atom, an amino group can be introduced by once introducing a nitro group, nitroso group, or azo group to the 4-position and reducing the compound by the method explained in item (1) above.

Practical synthesis examples of a compound represented by formula (I) will be described below.

EXAMPLE 1

Synthesis of Example Compound (3)

An example compound (3) was synthesized following a scheme presented below.

Synthesis of the Example Compound (3)

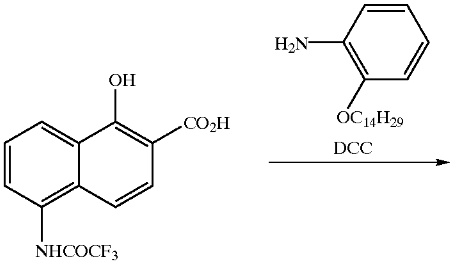

(3a)

-continued

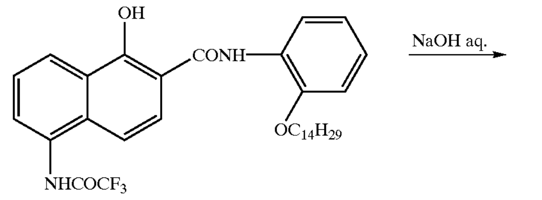

(3b)

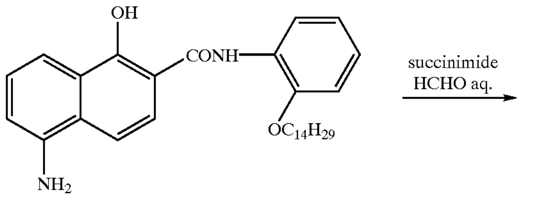

(3c)

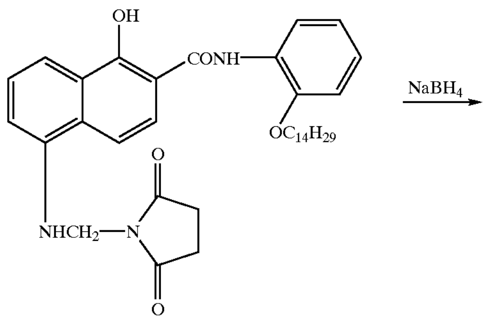

(3d)

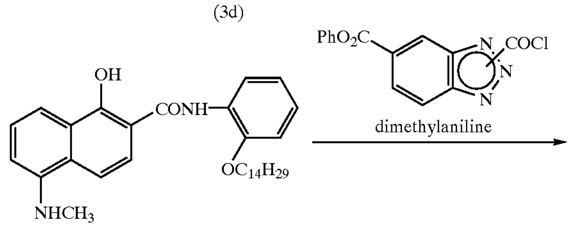

(3e)

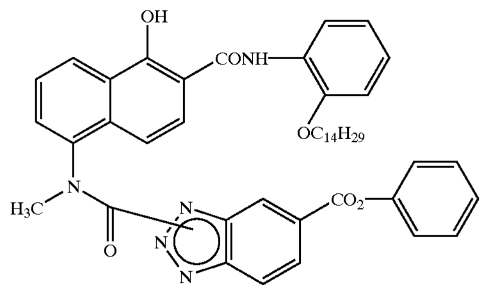

(3)

Synthesis of Compound 3b

An N,N-dimethylacetamide (60 mL) solution of dicyclohexylcarbodiimide (41.3 g) was dropped into an N,N-dimethylacetamide (250 mL) solution of a compound 3a (50 g) and o-tetradecyloxyaniline (51.1 g) at 30° C. The reaction solution was stirred at 50° C. for 1 hr, and ethyl acetate (250 mL) was added to cool the material to 20° C. After the reaction solution was filtered by suction, 1 N hydrochloric acid water (250 mL) was added to the filtrate to separate it. Hexane (100 mL) was added to the organic layer, and the precipitated crystal was filtered, washed with acetonitrile, and dried to obtain a compound 3b (71 g).

Synthesis of Compound 3c

An aqueous solution (150 mL) of sodium hydroxide (30 g) was dropped into a methanol (350 mL)/tetrahydrofuran (70 mL) solution of the compound 3b (71 g). The resultant solution was stirred in a nitrogen ambient at 60° C. for 1 hr. After the reaction solution was cooled to 20° C., concentrated hydrochloric acid was dropped until the system became acidic. The precipitated crystal was filtered, washed with water and acetonitrile, and dried to obtain a compound 3c (63 g).

Synthesis of Compound 3d

An ethanol solution (150 mL) of the compound 3c (20 g), succinimide (5.25 g), and 4.3 mL of an aqueous 37% formalin solution was stirred and refluxed for 5 hr. After the resultant material was cooled to 20° C., the precipitated crystal was filtered and dried to obtain a compound 3d (16 g).

Synthesis of Compound 3e

Sodium borohydride (1.32 g) was slowly added to a dimethylsulfoxide (70 mL) solution of the compound 3d (7 g) at 60° C. such that the temperature did not exceed 70° C. At that temperature, the resultant solution was stirred for 15 min. The reaction solution was slowly added to 1 N hydrochloric acid water (100 mL), and extraction was performed using ethyl acetate (100 mL). The organic layer was washed with water, dried by magnesium sulfate, and concentrated under reduced pressure. After the placing point components were removed by a short-path column (the eluting solvent: ethyl acetate/hexane=2/1), recrystallization was performed from the ethyl acetate/hexane system to obtain a compound 3e (3.3 g).

Synthesis of Compound (3)

A dichloromethane (100 mL)/ethyl acetate (200 mL) solution of phenoxycarbonylbenzotriazole (4.78 g) and N,N-dimethylaniline (2.42 g) was dropped into a dichloromethane (80 mL) solution of (trichloromethyl) carbonate (1.98 g). The resultant solution was stirred at 20° C. for 2 hr (a solution S).

120 mL of this solution S were dropped into a tetrahydrofuran (20 mL)/ethyl acetate (20 mL) solution of the compound 3e (2.0 g) and dimethylaniline (0.60 g) at 10° C. The resultant solution was stirred at 20° C. for 2 hr. The reaction solution was slowly added to 1 N hydrochloric acid water (200 mL), and extraction was performed using ethyl acetate (200 mL). The organic layer was washed with water, dried by magnesium sulfate, and concentrated under reduced pressure. After the resultant material was purified through a column (the eluting solvent: ethyl acetate/hexane=1/5), recrystallization was performed from the ethyl acetate/hexane system to obtain the example compound (3) weighting 1.3 g (m.p.=138–140° C.) (the compound was identified by elemental analysis, NMR, and mass spectrometry).

$^1$H NMR (300 MHz, $CDCl_3$); δ: 0.88(t,3H), 1.11–1.62 (22H), 1.90(m,2H), 3.73(s,3H), 4.10(t,2H), 6.85–9.07(18H), 13.81(s,1H). Elemental analysis; Calculated: C 71.76%, H 6.67%, N 9.10%, O 12.47%; Found: C 71.99%, H 6.76%, N 9.02%, O 12.23%.

EXAMPLE 2

Synthesis of Example Compound (41)

An example compound (41) was synthesized following a scheme presented below.

Synthesis of Example Compound (41)

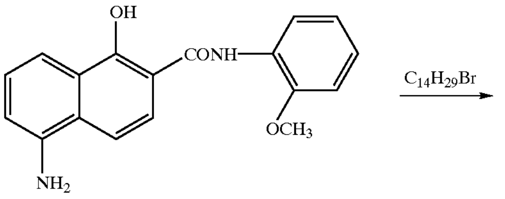

(41a)

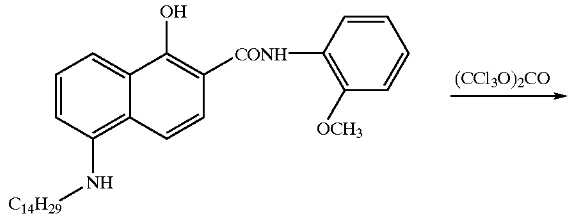

(41b)

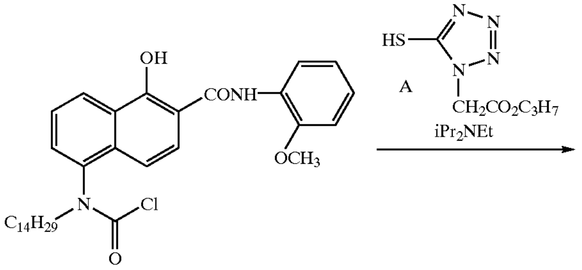

(41c)

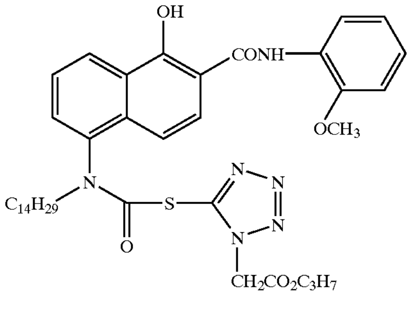

(41)

Synthesis of Compound 41b

A 1-methylpyrolidone (150 mL) solution of a compound 41a (50 g) synthesized following the similar procedure as for the compound 3c and bromotetradecane (78.6 g) was stirred at 120° C. for 5 hr, cooled to 25° C., and poured into ethyl acetate (600 mL)/water (600 mL). The organic layer was washed with water and concentrated under reduced pressure. The concentrated residue was recrystallized from the ethyl acetate/hexane system to obtain a compound 41b (48 g).

Synthesis of Compound 41c

A tetrahydrofuran (20 mL) solution of the compound 41b (6.5 g) and dimethylaniline (3.1 g) was dropped into a tetrahydrofuran (5 mL) solution of bis(trichloromethyl) carbonate (1.9 g) at 10° C. The reaction solution was stirred at 25° C. for 1 hr and poured into ethyl acetate (100 mL)/1 N hydrochloric acid water (100 mL). The organic layer was washed with water, dried with magnesium sulfate, and concentrated under reduced pressure. The concentrated residue was recrystallized from the ethyl acetate/hexane system to obtain a compound 41c (5.4 g).

Synthesis of Compound 41

A toluene (50 mL) solution of the compound 41c (3.0 g), a mercaptotetrazole derivative A (2.1 g), and N,N-diisopropyl-N-ethylamine (1.2 g) was stirred at 80° C. for 5 hr. The reaction solution was cooled to 30° C. and poured into ethyl acetate (100 mL)/sodium bicarbonate water (100 mL). The organic layer was washed with water, dried with magnesium sulfate, and concentrated under reduced pressure. The concentrated residue was purified through a column (the eluting solvent: ethyl acetate/hexane=1/2) to obtain the example compound (41) weighing 2.5 g (m.p.=104–105° C.) (the compound was identified by elemental analysis, NMR, and mass spectrometry).

$^1H$ NMR(300 MHz, $CDCl_3$); δ: 0.80(t,3H), 0.88(t,3H), 1.24(bs,24H), 1.57(m,4H), 3.40(m,1H), 4.00(s,3H), 4.08(t, 3H), 4.12(m,1H), 5.20(s,2H), 6.99(d,1H), 7.09(dd,1H), 7.18 (dd,1H), 7.37(d,1H), 7.59–7.67(m,2H), 7.71(d,$_1$H), 8.42(d, 1H), 8.63(d,1H), 8.82(s,1H), 13.82(s,$_1$H); Elemental analysis;

| | |
|---|---|
| Calculated: | C 63.91%, H 7.15%, N 11.47%, O 13.10%, S 4.38% |
| Found: | C 64.15%, H 7.24%, N 11.29%, O 13.02%, S 4.30% |

Synthesis of Example Compound (47)

An example compound (47) was synthesized following a scheme presented below.

Synthesis of Compound (47)

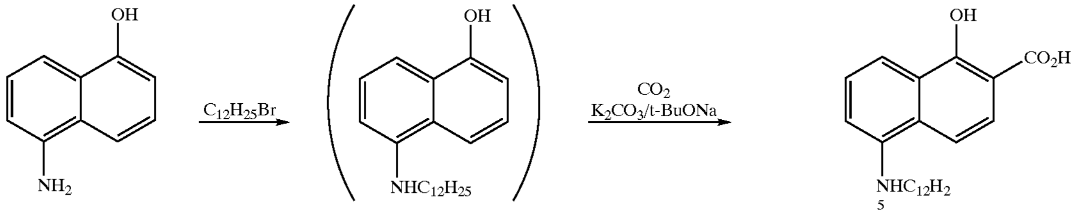

(47a) (47b) (47c)

-continued

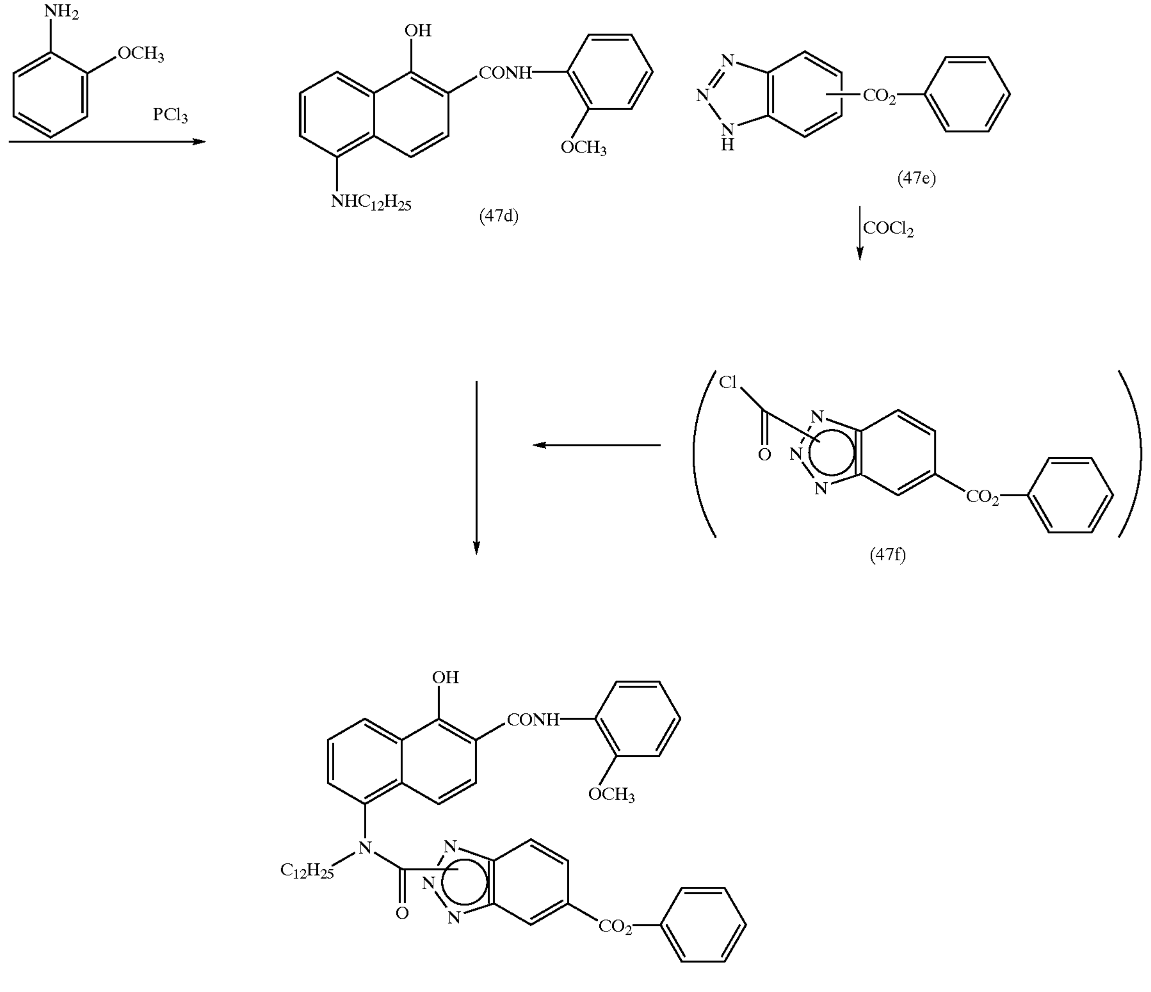

(47d) (47e) (47f) (47)

Synthesis of Compound 47c

A solution mixture of 5-amino-1-naphthol (Compound 47a (10 g)), n-dodecylbromide (17.2 g), sodium bicarbonate (5.8 g), and N-methylpyrrolidone (40 mL) was stirred in a nitrogen ambient at 130° C. for 5 hr and cooled to 50° C. Sodium t-butoxide (18.1 g) and potassium carbonate (26.0 g) were added to the obtained solution. The resultant solution was stirred in a 15-atm carbon dioxide ambient at 180° C. for 6 hr and cooled to 40° C. The obtained solution was poured into ethyl acetate (100 mL)/water (100 mL), and concentrated hydrochloric acid was added until the pH of the water layer became 8.5. Activated carbon (1 g) was added to the obtained solution mixture, and the resultant solution mixture was stirred for 15 min and filtered through celite. After the solution was separated, the organic layer was concentrated to approximately 50 mL and poured into water (70 mL)/concentrated hydrochloric acid (2.5 mL). Hexane (40 mL) was added to the obtained solution mixture, and the resultant solution mixture was cooled to 15° C. under slow stirring and left to stand for 30 min at that temperature. The crystal was filtered out, washed with ethyl acetate/hexane (=1/1) and acetone, and dried to obtain the compound 47c (14.3 g).

Synthesis of Compound 47d

A toluene (5 mL) solution of phosphorous trichloride (1.85 g): was dropped into a solution mixture of the compound 47c (10 g), o-anisidine (10 g), and toluene (50 mL), and the resultant solution was stirred at 60° C. for 4 hr. Water (50 mL)/methanol (5 mL) was added to the obtained solution, and the solution was separated at 50° C. Water (50 mL)/methanol (5 mL) was further added to the organic layer, and the resultant solution was separated at 50° C. Activated carbon (0.5 g) was added to the organic layer, and the resultant material was stirred at 70° C. for 15 min and filtered through celite. The filtrate was stirred at 5° C. for 1 hr. The obtained crystal was filtered out, washed with toluene, and dried to obtain the compound 47d 9.5 g).

Synthesis of Compound (47)

A solution mixture of a compound 47e (5.3 g), phosgene (4.3 g), and toluene (30 mL) was stirred at 40° C. for 3 hr. The excess phosgene was removed to obtain a toluene solution of a compound 47f.

This toluene solution of the compound 47f was dropped into a solution mixture of the compound 47d (10 g), sodium bicarbonate (2.64 g), and toluene (50 mL) at 10° C. or less.

After the reaction solution was stirred at 25° C. for 2 hr, 10 mL of methanol were added, and the resultant solution was further stirred at 40° C. for 1 hr. The reaction solution was washed with an aqueous 5% sodium carbonate solution (50 mL), concentrated hydrochloric acid (5 mL)/water (50 mL), and water (50 mL) and concentrated under reduced pressure. The concentrated residue was recrystallized from ethyl acetate/methanol to obtain the example compound (47) weighing 15.0 g (m.p.=99–103° C.) (the compound was identified by elemental analysis, NMR, and mass spectrometry).

$^1H$ NMR(300 MHz, $CDCl_3$); δ: 0.89(t,3H), 1.24(bs,18H), 1.85(bs,2H), 3.73(s,1H), 3.95(s,3H), 4.36(m,1H), 6.89–9.00 (18H), 13.71(s,1H); Elemental analysis; Calculated: C 71.24%, H 6.38%, N 9.44%, O 12.94%; Found: C 71.59%, H 6.08%, N 9.22%, O 13.11%.

Compounds set forth in Table 1 were synthesized in the similar manner as above.

TABLE 1

| Compound No. | Melting point (° C.) |
|---|---|
| (10) | 156–157 |
| (12) | 161–163 |
| (13) | 111–113 |
| (14) | 77–81 |
| (16) | 96–98 |
| (18) | 78–84 |
| (19) | 119–129 |
| (20) | 95–97 |

A practical method of regenerating a compound (AH) having an acidic proton from a compound of the present invention will be described below.

EXAMPLE 3

Reduction of Azo Dye of Compound Example (34)

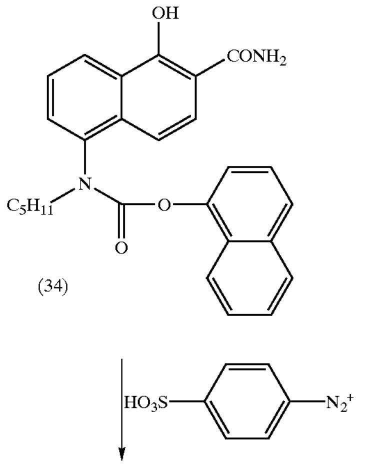

(34)

-continued

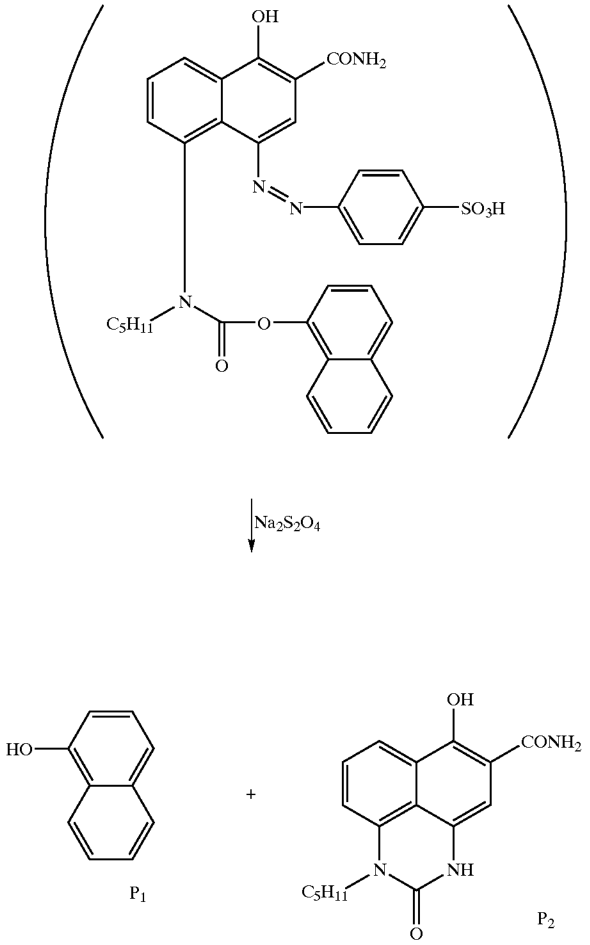

P1 + P2

4.8 g of sulfanyl acid were dispersed in 30 mL of water, 1.25 g of sodium hydroxide were added, and the resultant solution was stirred. Subsequently, 8.1 mL of hydrochloric acid were added, the resultant material was cooled to −5° C., and an aqueous sodium nitrite solution (1.4 g/5 mL) was slowly dropped. The resultant material was stirred at 0° C. for 30 min to prepare a solution of diazonium salt. 10 g of the compound (34) were dissolved in 100 mL of methanol, 2.8 g of sodium hydroxide, and 50 mL of water, and the solution of diazonium salt was dropped into the resultant solution. After the resultant solution mixture was stirred at room temperature for 1 hr, 50 g of hydrosulfite soda were gradually added, and the resultant material was stirred at 40° C. for 30 min. The reaction solution was poured into 1 L of ethyl acetate and 1 L of water. The organic layer was further washed with water three times, dried with magnesium sulfate, and concentrated under reduced pressure. The concentrated residue was purified by column chromatography (the eluting solvent: ethyl acetate/hexane=1/1 to 2/1) to obtain a compound $P_1$ weighing 2.9 g (90%) and a compound $P_2$ weighing 5.7 g (80%).

EXAMPLE 4

Reaction of Example Compound (47) with p-Phenylenediamine in an Oxidized Form

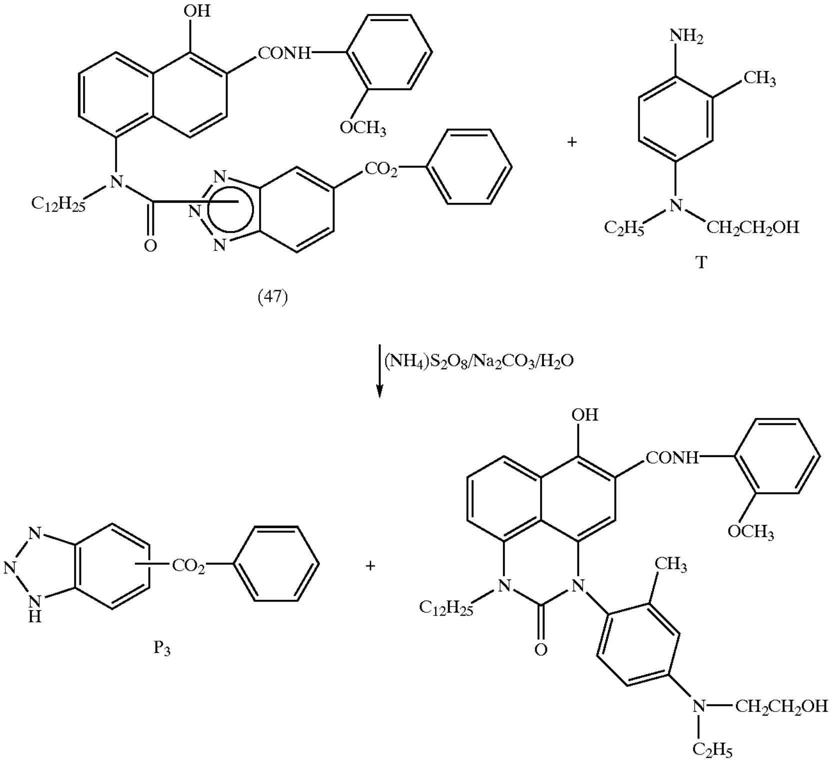

(47) T $P_3$ $P_4$

A solution prepared by dissolving 4.61 g of ammonium persulfate and 25.6 g of sodium carbonate in 200 mL of water was dropped into a dispersion of tetrahydrofuran (450 mL)/diethyl ether (450 mL) 10 containing 10 g of the compound (47) and 5.12 g of sulfate of a compound T over 30 min. The resultant solution was stirred at a room temperature for 30 min. The reaction solution was poured into ethyl acetate (360 mL)/dilute hydrochloric acid water (400 mL) and separated. The organic layer was washed with dilute hydrochloric acid water five times and with an aqueous sodium bicarbonate solution three times, dried with magnesium sulfate, and concentrated under reduced pressure. The concentrated residue was purified by column chromatography (the eluting solvent: ethyl acetate/hexane=1/1 to 2/1) to obtain a compound $P_3$ weighing 3.0 g (93%) and a compound $P_4$ weighing 7.6 g (81%).

Reactions were performed following the same procedures as in the above reaction example except that equal molar amounts of the example compounds (22), (27), (37), (39), (42), and (58) described above were used instead of the example compound (47). The main products of the reactions and their yields are summarized below.

| Example compound | Main product (yield %) | |
|---|---|---|
| (22) | 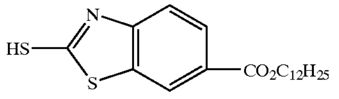 (85%) | 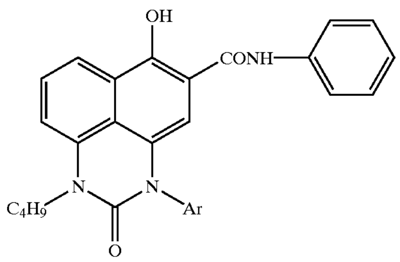 (81%) |

-continued
| Example compound | | Main product (yield %) |
|---|---|---|
| (27) | 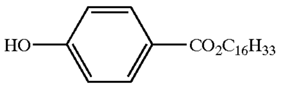<br>(95%) | 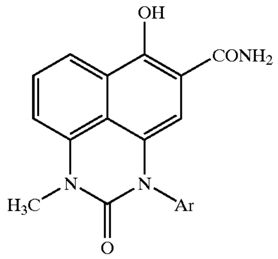<br>(84%) |
| (37) | 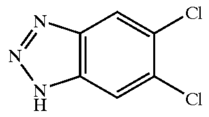<br>(92%) | 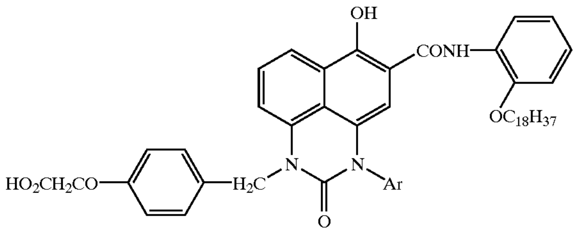<br>(80%) |
| (39) | 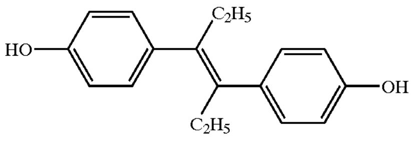<br>(88%) | 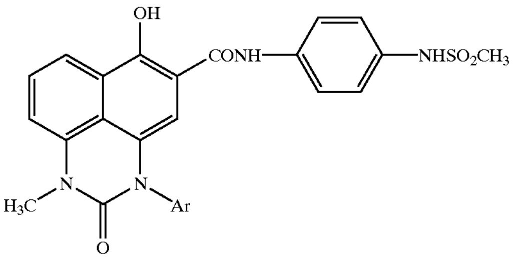<br>(76%) |
| (42) | 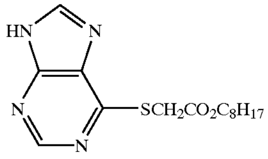<br>(93%) | 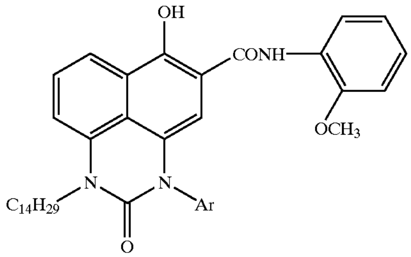<br>(84%) |
| (58) | 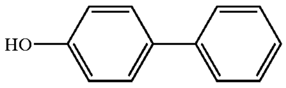<br>(90%) | 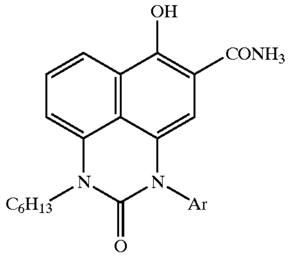<br>(77%) |

-continued

| Example compound | Main product (yield %) |
| --- | --- |

Ar = 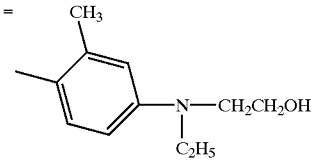

Also, 4 mL of a buffering solution of pH=11.5 were added to 6 mL of a 0.0027 mol/L tetrahydrofuran solution of the compound (47), and the resultant solution mixture was stirred at 25° C. for 6 hr. Consequently, the residue ratio of the compound (47) was 51%. However, the decomposition was solely hydrolysis of the phenyl ester portion, and no generation of a deblocked benzotriazole derivative was found.

Examples 1 to 4 show that a compound of the present invention can be readily synthesized, at least a blocked portion is stable under alkali hydrolysis conditions, and a compound having an acidic proton or the dissociated form of the compound can be rapidly released by introducing a certain nucleophilic substituent to the 4-position of naphthol.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A 1-naphthol compound represented by formula (II) below:

(II)

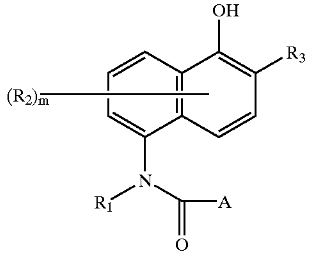

wherein A represents a 6- to 32-carbon substituted or nonsubstituted aryloxy group, a 1- to 32-carbon substituted or nonsubstituted heterocyclic oxy group, a 1- to 32-carbon substituted or nonsubstituted alkylthio group, a 6- to 32-carbon substituted or nonsubstituted arylthio group, a 1- to 32-carbon substituted or nonsubstituted heterocyclic thio group, a 1- to 32-carbon substituted or nonsubstituted azole group, or a 2- to 32-carbon substituted or nonsubstituted carbonyloxy group; $R_1$ represents an aliphatic group, aryl group, or heterocyclic group; $R_2$ represents a substituent; $R_3$ represents a halogen atom, cyano group, $R_{12}$ (R13)NCO—, or $R_{12}CON(R_{13})$—, m represents an integer of 0 to 4; and each of $R_{12}$ and $R_{13}$ independently represents a hydrogen atom, aliphatic group, aryl group, or heterocyclic group.

2. A process for preparing a compound having an acidic proton represented by AH through an intramolecular nucleophilic reaction by introducing a nucleophilic group to the 4-position of the 1-naphthol compound represented by formula (II) of claim 1.

3. The 1-naphthol compound according to claim 1, wherein A is an aryloxy group.

4. The 1-naphthol compound according to claim 1, wherein A is an arylthio group.

5. The 1-naphthol compound according to claim 1, wherein A is a heterocyclic oxy group.

6. The 1-naphthol compound according to claim 1, wherein A is a heterocyclic thio group.

7. The 1-naphthol compound according to claim 1, wherein A is an azole group.

8. The 1-naphthol compound according to claim 1, wherein the 1-naphthol compound is represented by formula (III) below:

(III)

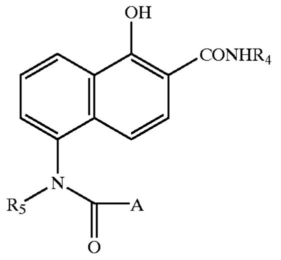

wherein $R_4$ represents a hydrogen atom or a group having the same meaning as $R_1$ of claim 1; $R_5$ represents an aliphatic group having 1 to 32 carbon atoms; and A has the same meaning as defined in claim 1.

9. The 1-naphthol compound according to claim 8, wherein A is an aryloxy group.

10. The 1-naphthol compound according to claim 8, wherein A is an arylthio group.

11. The 1-naphthol compound according to claim 8, wherein A is a heterocyclic oxy group.

12. The 1-naphthol compound according to claim 8, wherein A is a heterocyclic thio group.

13. The 1-naphthol compound according to claim 8, wherein A is an azole group.

14. The 1-naphthol compound according to claim 8, wherein A is an arylthio group.

15. The 1-naphthol compound according to claim 8, wherein A is a heterocyclic thio group.

16. The 1-naphthol compound according to claim 8, wherein A is an azole group.

17. A process for preparing a compound having an acidic proton represented by AH through an intramolecular nucleophilic reaction by introducing a nucleophilic group to the 4-position of the 1-naphthol compound represented by formula (III) of claim 8.

18. The process according to claim 17, wherein A is a heterocyclic thio group.

* * * * *